United States Patent [19]

Bachand

[11] Patent Number: 5,091,153
[45] Date of Patent: Feb. 25, 1992

[54] CHEMICAL ANALYSIS TEST DEVICE

[75] Inventor: Steve S. Bachand, Laguna Niguel, Calif.

[73] Assignee: Toxi-Lab Incorporated, Irvine, Calif.

[21] Appl. No.: 595,976

[22] Filed: Oct. 11, 1990

[51] Int. Cl.⁵ .............................................. G01N 31/22
[52] U.S. Cl. .................................... 422/58; 422/56; 422/61; 422/101; 422/102; 436/808; 436/810; 435/810
[58] Field of Search ..................... 422/56–58, 422/61, 101, 102, 78; 436/808, 810; 435/295, 810

[56] References Cited

U.S. PATENT DOCUMENTS

| | | |
|---|---|---|
| 3,582,285 | 6/1971 | Hamilton . |
| 3,888,628 | 6/1975 | Graham . |
| 4,154,793 | 5/1979 | Guigan . |
| 4,780,280 | 10/1988 | Berger et al. . |
| 4,789,629 | 12/1988 | Baker et al. . |

Primary Examiner—Robert J. Warden
Assistant Examiner—Lyle A. Alexander
Attorney, Agent, or Firm—Knobbe, Martens, Olson & Bear

[57] ABSTRACT

A chemical analysis test device for detection of a selected chemical in a biological fluid is disclosed wherein the test is preformed on a rigid base containing a detection well for holding a reagent and a specimen well for holding a sample of the biological fluid to be tested. The detection well is positioned above a concentration chamber wherein the cross-sectional area of the chamber increases as the distance from the bottom of the detection well increases. A passage connects the concentration chamber to the detection well. The specimen well has a generally hemispherical interior surface and has an opening in the bottom thereof. A strip of wicking material is secured to the base interconnecting the opening in the specimen well and the concentration chamber. A specimen of the biological fluid to be tested is deposited in the specimen well and contacts the wicking material through the opening in the bottom of the well. The wicking paper wicks the specimen across to the concentration chamber and is treated with an agent to volatilize the chemical under test. The volatilized chemical is concentrated by the concentration chamber and forced through the passage into contact with the reagent stored in the detection well, producing a visible color change in the detection well above the passage, indicative of the chemical content in the biological fluid.

13 Claims, 4 Drawing Sheets

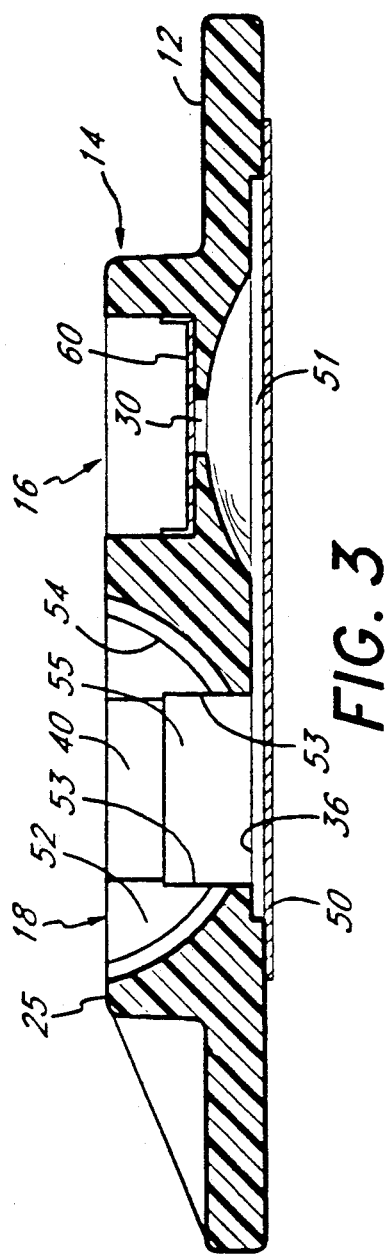
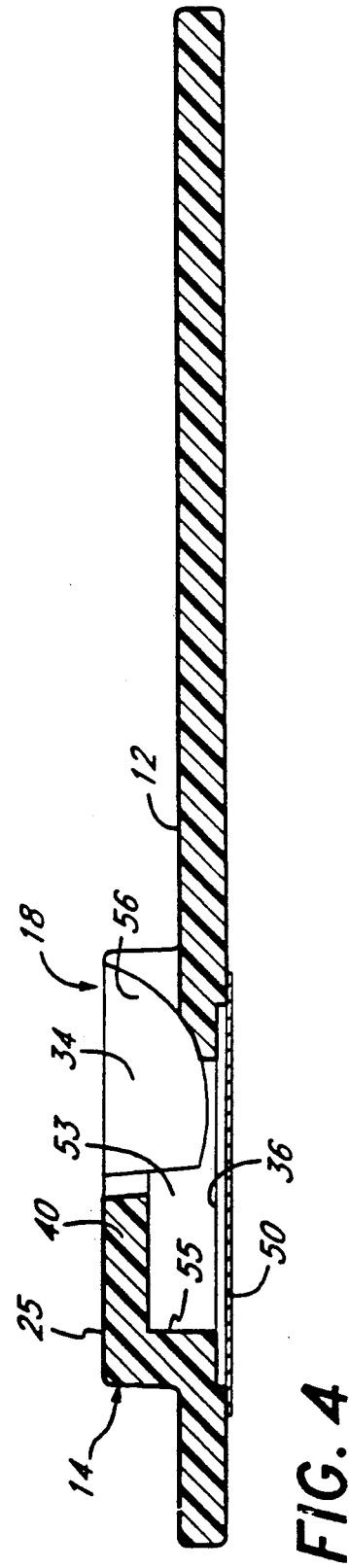

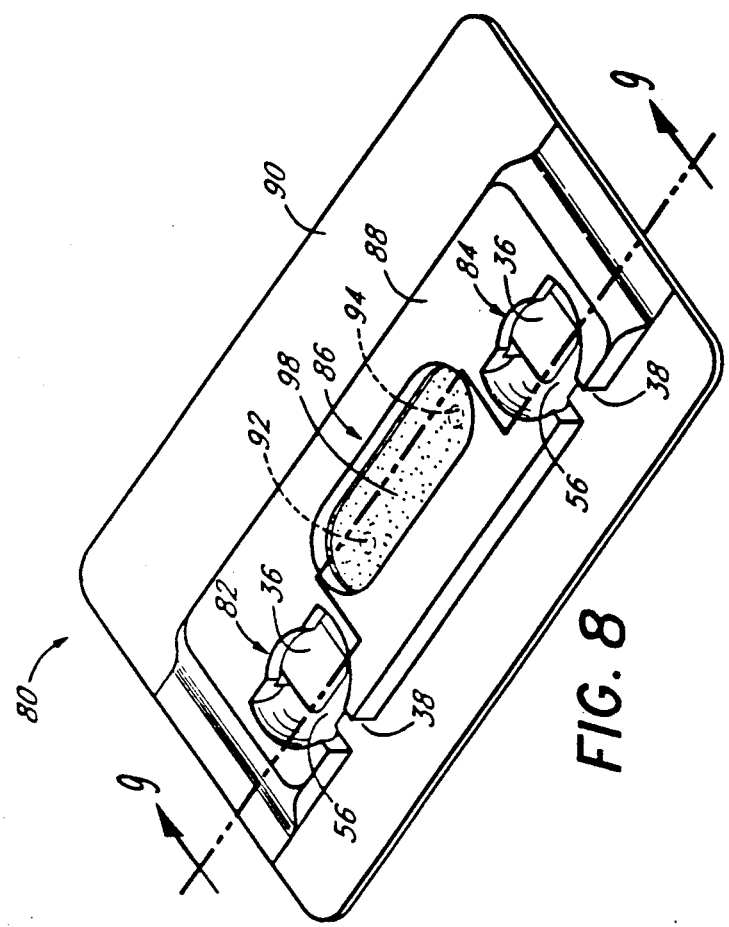
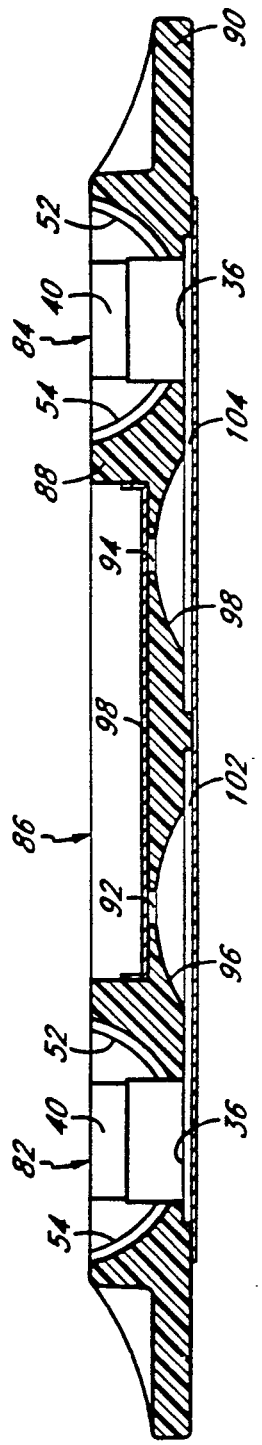
FIG. 8
FIG. 9

CHEMICAL ANALYSIS TEST DEVICE

FIELD OF THE INVENTION

The invention relates to chemical analysis tests, and, in particular, to a colorimetric test device for determining the presence of a chemical in a biological specimen.

BACKGROUND OF THE INVENTION

Chemical analysis tests are commonly utilized by policemen, parole officers, and other law enforcement personnel to determine if a person has been drinking. Often, the tests are used as screening devices to qualitatively indicate the presence of alcohol. Typically, a breath sample, or a sample of a bodily fluid, such as saliva, or blood, is taken and then chemically analyzed for alcohol content. If it is found that alcohol is present in the sample, additional, more sophisticated tests can be performed in clinical or lab environments to measure the actual amount or percentage of alcohol in the body.

In these types of chemical analysis tests, the test is commonly designed to be performed on a single type of sample. For example, tests utilizing breath samples are frequently used by police officers and highway patrol officers to test for drunk driving, while tests utilizing saliva or blood samples are often utilized in clinical environments and laboratory settings. In situations where it is inconvenient or difficult to obtain the required fluid, such as testing performed in the field, or in situations where the person under test has a legal right to choose the means of testing, typically breath analysis, urinalysis, or blood testing, there are often no readily available alternative or convenient testing means. Additionally, it is often necessary for law enforcement offices to stock several different types of chemical analysis tests for the laboratory and field environments, as well as for each type of biological fluid which may be tested.

Further, such tests often require heat or diffusion methods to perform the chemical analysis, thereby increasing both the mechanical complexity of the test device, as well as the amount of time necessary to perform the test and detect the results. In addition, many test devices require comparatively large samples of biological fluids which can be difficult to obtain in some circumstances. These complex equipment requirements and involved chemical analysis processes often prevent testing in the field where speed, portability, and simplicity are foremost concerns.

SUMMARY OF THE INVENTION

The present invention provides a test for the rapid detection of a selected chemical in a biological specimen, wherein the test can be advantageously performed using one of several types of biological fluids, thus providing increased flexibility and versatility over previous chemical test devices. In the test procedure, a volatile component, or components, of a specimen of the biological fluid to be tested is brought into contact with a reagent. Any amount of the chemical under test contained in the specimen will reduce the reagent, producing a visible color change indicative of the chemical content.

In accordance with the present invention, a unique apparatus and testing method are disclosed wherein the test is performed on a rigid base. The base includes a platform containing a first well used for containing the specimen of the biological fluid to be tested, and a second well used to hold the detection reagent. The detection well is concentrically located above a concentration chamber. At the top of the concentration chamber is a passage which links the chamber to the detection well. Advantageously, the concentration chamber decreases in cross-sectional area as the distance from the bottom of the chamber increases.

The specimen well is at least partially formed by the surfaces of the base and which includes a bottom surface which defines an opening. The well is sized and shaped so as to wring biological fluid form the head of a swab inserted therein. Advantageously, the well includes an upper shelf for compressing the head of a swab as the swab is inserted into the first well under the shelf thereby releasing the biological fluid deposited on the head of the swab. Additionally, the specimen well is advantageously provided with a notch formed opposite the shelf for receiving and retaining the handle of the swab to lock the swab in place after the head of the swab has been inserted into the first well under the shelf. A strip of chemically treated wicking material is secured to the base interconnecting the opening in the specimen well and the concentration chamber. The material forms the bottom of the concentration chamber.

The chemical test device of the present invention can be performed on a fluid sample as small as 100 $\mu$L, thus enabling the test to be easily performed in the field without complex extraction procedures. Once the biological fluid under test has been deposited inside the specimen well, it contacts the chemically treated paper via the opening inside the well and the fluid is wicked across the strip of wicking material to the concentration chamber. The strip is pre-treated with a chemical which volatilizes the chemical under test so that the rising vapors of the chemical sought to be detected are concentrated by the concentration chamber and are directed through the passage where they contact the reagent stored in the reagent well. Thus, if the biological fluid contains the chemical under test, the volatilized chemical reduces the reagent and produces a visible color change in the detection well. The entire test process is performed on the base, and requires no additional equipment or analysis processes.

In one embodiment of the invention, a specimen of saliva is taken on an absorbent swab having a foam head and a handle. The swab is placed directly in the mouth and saturated to obtain the specimen. The saturated swab is then inserted in the detection well by placing the head beneath the shelf, such that the saliva is discharged from the swab onto the chemically treated paper beneath the opening in the well. The swab is then secured for the duration of the test by fitting the handle within the notch provided in the well.

An alternative embodiment of the test device incorporates two specimen wells, one for use with a specimen of a biological fluid to be tested, and the other for use with a control specimen. A detection well having a flat, bottom surface is located between the two specimen wells and includes first and second concentration chambers located at opposite ends of the well. Desirably, each concentration chamber has a cross-sectional area which decreases as the distance from the bottom surface of the concentration chamber increases. A first strip of wicking material is affixed on the underside of the base and positioned beneath the control specimen well and first concentration chamber. A second strip of wicking material is positioned beneath the biological specimen well and the second concentration chamber. Each concentration chamber has a small cylindrical passage linking the concentration chambers to the detection well. The chemical under test contained in either specimen is volatilized by the chemical contained in the paper and brought into contact with the reagent, producing a visible color change above the passage adjacent the corresponding specimen well. Comparison of the effect of the volatilized test specimen and the effect of the volatilized control specimen on the reagent can then be compared to help evaluate the validity of the test results.

BRIEF DESCRIPTION OF THE DRAWINGS

FIG. 3 is a cross-sectional view of the test device taken along lines 3—3 of FIG. 1;

FIG. 4 is a cross-sectional view of the test device taken along lines 4—4 of FIG. 1;

FIG. 8 is a perspective view of an alternative embodiment of the test device of the present invention;

FIG. 9 is a cross-sectional view of the test device taken along lines 9—9 of FIG. 8.

DETAILED DESCRIPTION OF THE INVENTION

Figure 1:
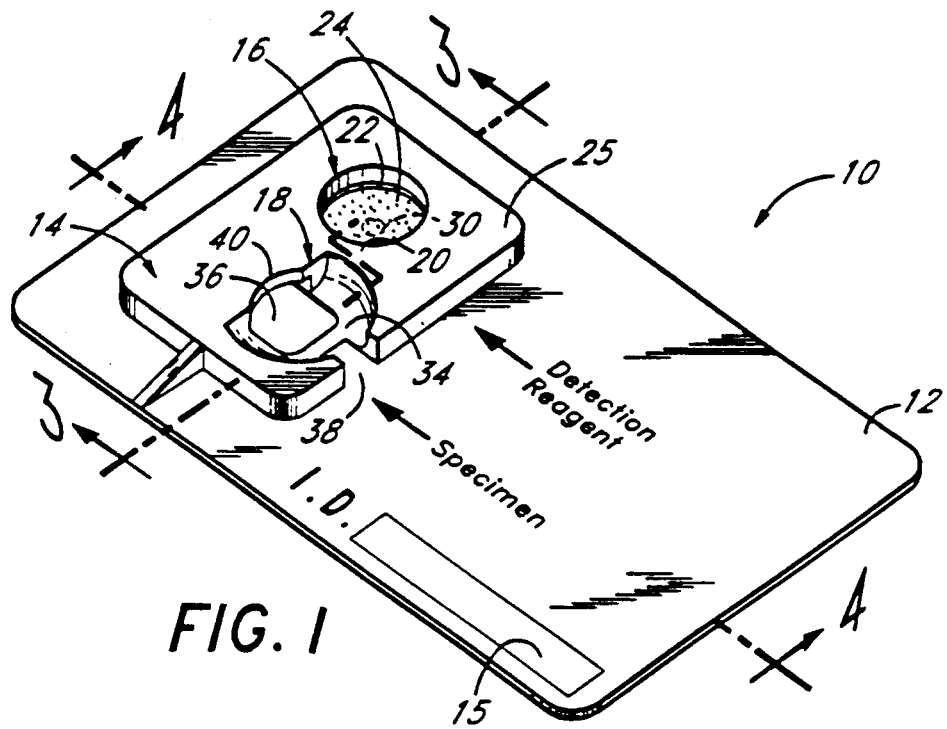
FIG. 1 is a top perspective view of the preferred embodiment of the chemical analysis test device of the present invention.
Figure 2:
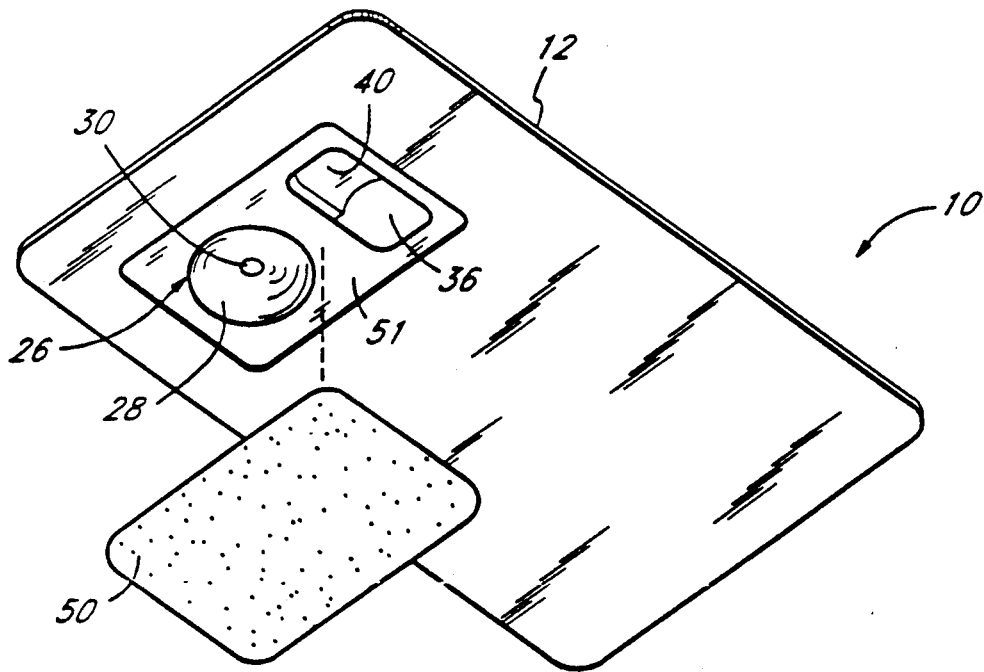
FIG. 2 is a bottom perspective view of the test device with the wicking paper removed to show greater detail.

FIG. 1 and FIG. 2 are perspective views of a chemical analysis test device 10 in accordance with the present invention. The test device 10 has a base 12 having a raised area or platform 14 formed thereon. The base 12 further includes an identification region 15 for recording information such as a name or number to identify the test. The platform 14 contains a first or specimen well 18 used to hold a sample or specimen, and a second or detection well 16 used to hold detection reagent. As illustrated, markings are provided on the base 12 adjacent each well 16, 18 so as to indicate the well content. The platform 14 further provides a common wall 20 which separates the detection and specimen wells. The detection well 16 is generally cylindrical, being defined by a cylindrical vertical outer wall 22 and a flat circular bottom 24. Located concentrically beneath the detection well 16 is a dome shaped concentration chamber 26 defined by a generally hemispherical surface 28. Although the hemispherical surface 28 has been found to be particularly desirable, the concentration qualities of the chamber 26 will function so long as the shape of the chamber 26 is such that the cross-sectional area of the chamber 26 decreases as the distance from the bottom of the chamber 26 to the location where the cross-section is being measured increases, wherein the cross-section is taken in a plane parallel to the base 12. At the top and center of the concentration chamber 26 is a small cylindrical passage 30 linking the concentration chamber 26 to the detection well 16.

The specimen well 18 is generally concave, being defined by a generally hemispherical surface 34 in the bottom of which is a rectangular opening 36. Additionally, the specimen well 18 has an opening or notch 38 which extends the height of the platform 14 and tapers in width from a top surface 25 of the platform 14 to the base 12. A shelf 40 coplanar with the top surface 25 of the platform 14 extends from the side of the well 18 opposite the notch 38 over approximately one-half of the length of the rectangular opening 36 in the bottom of the well 18. A strip of wicking material 50, such as glass fiber paper, is affixed to the underside of the base 12 beneath the platform 14 within a recess 51 positioned beneath the concentration chamber 26 and the rectangular opening 3 in the specimen well 18.

The configuration of the specimen and detection wells 16, 18 is illustrated in more detail in the enlarged cross-sectional views of FIG. 3 and FIG. 4. The specimen well 18 comprises first and second generally hemispherical walls 52, 54 which begin at the top surface 25 of the platform 14 and curve downwardly, terminating at the rectangular opening 36. The shelf 40 and notch 38 are located opposite one another between the hemispherical walls 52, 54 of the well 18. The shelf 40 is formed by the projection of the top surface 25 of the platform 14 over the interior 34 of the well 18, such that the shelf 40 is coplanar with the top surface 25 of the platform 14. Additionally, the shelf 40 extends over approximately one-half of the rectangular opening 36 formed at the bottom the well 18. Two substantially vertical walls, generally designated 53, extend above the rectangular opening 36 in the well 18 and support the shelf 40 above the interior of the well 18. A third vertical wall 55 extends above one end of the opening 36, opposite the notch 38, and defines the end of the shelf 40. As described above, the notch 38 in the specimen well 18 extends through the height of the platform 14 and terminates on the base 12, tapering in width from the top surface 25 of the platform 14 to the base 12. A third curved wall 56 connects the rectangular opening 36 in the bottom of the well 18 to the notch 38.

The cylindrical passage 30 connecting the concentration chamber 26 to the well 16 is centered with respect to the flat bottom surface 24 of the well 16 and is covered with a reagent retaining material, such as a circular piece of inert glass fiber paper 60. The concentration chamber 26 extends above the surface of the strip of glass fiber paper 50 placed in the recess 51 on the underside of the base 12. As will be explained in detail below, a chemical under test contained in a specimen deposited in the specimen well 18 is wicked across the strip of glass fiber paper 50 affixed to the bottom of the base 12 and focused up through the passage 30 into contact with a reagent contained in the detection well 16.

Preferably, the base 12, including platform 14, and wells 16, 18, is formed of a rigid plastic material such as Polystyrene, manufactured by Dow Corning Corporation of Midland, Mich. The spherical radius of the concentration chamber 26 is preferably constructed as 0.406 inches and the diameter of the passage 30 connecting the concentration chamber 26 to the well 16 is approximately 0.078 inches. Preferably the width of the shelf 40 is 0.430 inches and the length is 0.58 inches. The spherical radius of the walls 52, 54, 56 in the specimen well 18 is preferably 0.281 inches.

Figure 5:
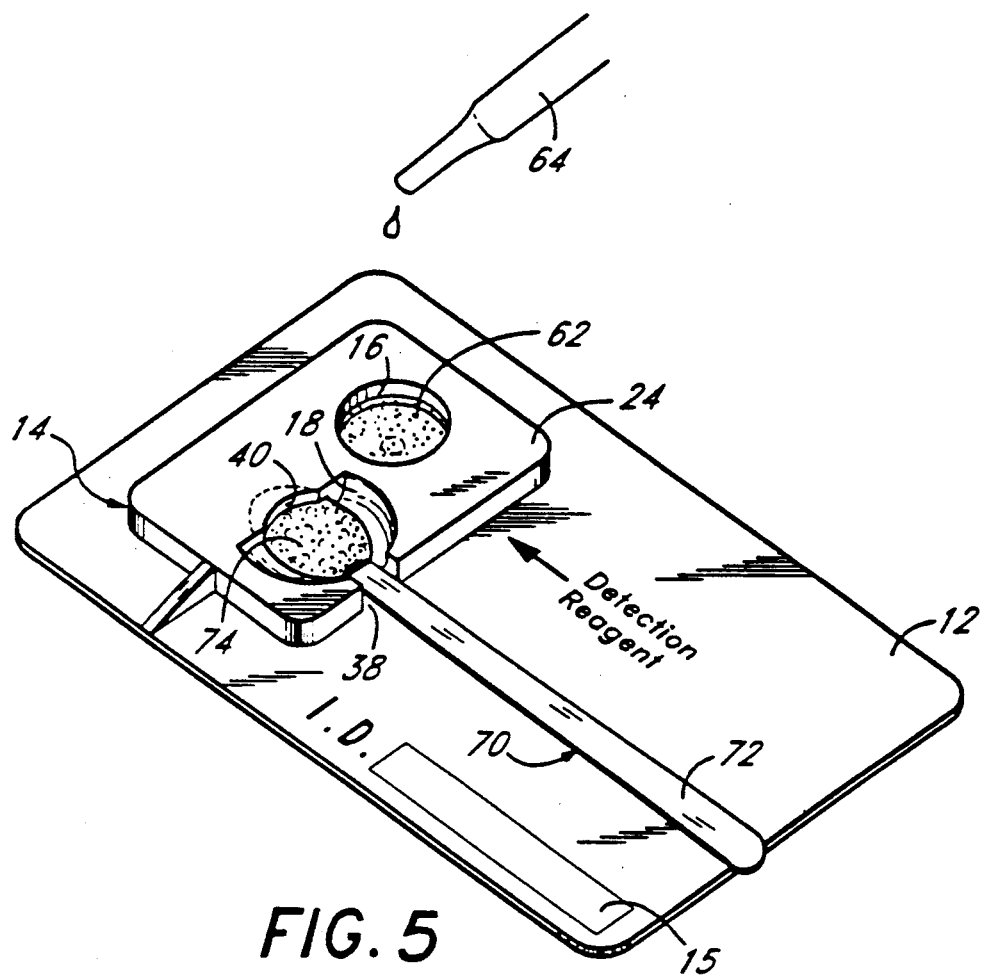
FIG. 5 illustrates alternative methods of using the device of FIG. 1.

Referring to FIG. 5, in operation, preferably 40 $\mu$L of a liquid reagent 62 is deposited into the detection well 16. Preferably, the reagent is sealed in a crush ampule (not shown) enclosed in a dropper 64, however, a pipet, or any other suitable liquid transfer means could also be used to deposit the reagent in the detection well 16. Preferably, the reagent 62 comprises chromium trioxide for the detection of alcohol in a specimen, although, one skilled in the art will recognize that a wide variety of chemical compounds could be used to detect a variety of chemicals and produce a colorimetric reaction in accordance with the present invention. Inside the detection well 16, the liquid reagent 62 is absorbed into the glass fiber paper 60 placed over the bottom surface 30 of the well 16. After the reagent 62 has been deposited within the well 16 and absorbed by the paper 60, a sample of the biological fluid under test, in the form of a specimen of saliva, serum, or urine, is deposited in the specimen well 18.

To transfer a saliva specimen to the specimen well 18, a swab 70 comprising a handle 72 and a generally circular absorbent foam head 74 is used. The swab 70 is placed directly into the mouth of person to be tested and the foam head 74 is saturated with saliva. The swab 70 is then placed beneath the shelf 40 inside the specimen well 18. The width of the shelf 40 is advantageously selected to be smaller than the diameter of the foam head 74 of the swab 70, so as to compress the head 74 beneath the shelf 40 and between the vertical walls 53 in the well 18. The swab 70 is then secured in position for the duration of the test by aligning the handle 72 with the notch 38 provided in the specimen well 18 and applying pressure such that the handle 72 is forced downward into the tapered slot near the base 12 and snap fit within the notch 38. When inserted in this manner, the sides of the foam head 74 of the swab 70 are compressed beneath the shelf 40 between the vertical walls 53 and the saliva saturating the swab 70 is squeezed or wrung out of the head 74 and discharged onto the glass fiber paper 50 via the rectangular opening 36 in the well 18.

Alternatively, a specimen of urine, saliva, or serum may be deposited directly into the specimen well 18 using a pipet or conventional fluid transfer means. Desirably, approximately 100 $\mu$L of the specimen is dispensed directly into the specimen well 18 where it is directed toward the opening 36 in the bottom of the well 18 by the hemispherical walls 52, 54. Due to the high viscosity of saliva, three discrete drops may be difficult to dispense, and, in this situation, the well 18 may be filled with saliva until approximately one-quarter full.

Once inside the specimen well 18, the specimen of biological fluid, in any of the above-noted forms, contacts the glass fiber paper 50 through the rectangular opening 36 in the bottom of the specimen well 18. The paper 50 wicks the specimen from the opening 36 toward the detection well 16. The glass fiber paper 50 preferably comprises inert HEPA paper and is chemically treated with an agent to change the solubility of the specimen, volatilizing the specimen directly from the strip 50. Preferably, when the test is for the presence of alcohol, the strip of glass fiber paper 50 is impregnated with potassium carbonate. However, as one skilled in the art will recognize, a variety of chemical compounds could be used to produce this type of volatilization depending upon the chemical under test.

As described above, the specimen is wicked across the strip of paper 50 from the specimen well 18 toward the detection well 16. Beneath the detection well 16, the rising vapors created in the volatilization process are forced upward and inward by the decreasing cross-sectional area of the concentration chamber 26 approaching the bottom 24 of the detection well 16 and are forced out through the passage 30. Alcohol, including ethanol, methanol, and isopropanol, volatilized from the specimen will reduce the reagent saturated in the paper 60 positioned over the passage 30, producing a visible color change in the area of detection well 16 directly over the passage 30. The selective volatilization of alcohol from the specimen eliminates interfering substances and conditions which can negatively influence results of other test methods, i.e., enzyme tests. Acetone, Vitamin C, and elevated sample pH are examples of interfering substances and conditions that can produce false-negative or false-positive results.

Figure 6:
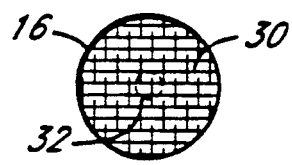
FIG. 6 and FIG. 7 illustrate the chemical reactions which occur.
Figure 7:
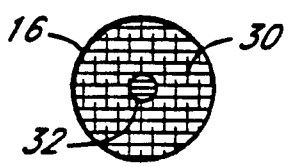

FIG. 6 illustrates the detection well 16 after the reagent has been deposited and absorbed by the paper 60 positioned over the flat bottom surface 24 of the well 16. As discussed above, the reagent preferably comprises chromium trioxide. The chromium trioxide is generally yellow in color and produces an area of solid yellow over the entire bottom surface 24 of the well 16, including the passage 30 (shown in phantom). Once the specimen has been deposited in the specimen well 18 and volatilization of the specimen occurs in the manner described above, alcohol vapors contained in the specimen are brought into contact with the reagent through the passage 30 in the bottom surface 24 of the detection well 16. When the yellow chromium trioxide is exposed to alcohol vapor, it is reduced to blue chromic oxide, thus producing a visible color change in the detection well 16 above the passage 30 as illustrated in FIG. 7. Thus, when alcohol is present in the specimen, a blue spot will appear above the passage 30 in the bottom surface 24 of the detection well 16, providing an easy to read indicator of alcohol content in the biological fluid under test. Conversely, when no alcohol is present in the specimen, no color change is produced and the detection well 16 remains the solid yellow color shown in FIG. 6.

Thus, the alcohol test device 10 of the present invention provides a simple method and apparatus for the rapid colorimetric detection of a given chemical in a variety of biological fluids. Advantageously, the above process produces results within three minutes after depositing the specimen within the specimen well 18. Furthermore, the test device 10 is sensitive to alcohol concentrations as low as 0.02 w/v. The device 10 can be easily used in clinical laboratory settings, as well as in field testing applications where minimal equipment requirements and carrying ease are foremost concerns.

FIG. 8 and FIG. 9 illustrate an alternative embodiment of a test device 80 in accordance with the present invention comprising a control well 82, a specimen well 84, and a detection well 86 contained in a platform area 88 formed on a base 90. This embodiment is particularly useful in clinical lab situations where it is often desired to run a control experiment with each test for alcohol content. The control well 82 and specimen well 84 are identical to the specimen well 18 described in connection with FIGS. 1-5 and are numbered correspondingly. As described above, each well 82, 84 includes hemispherical walls 52, 54, a curved wall 56, a shelf 40 formed by the platform 90, a notch 38, and a rectangular opening 36. Preferably, the wells 82, 84 are constructed with the same dimensions given above for the specimen well 18.

Connecting the detection well 86 to the first and second concentration chambers 96, 98 are a first and second cylindrical passage 92, 94 located at opposite ends of the well 86. A layer of reagent retaining material, such as glass fiber HEPA paper 98 lines the detection well 86, overlying the passages 92, 94. The concentration chambers 96, 98 are identical to the concentration chamber 30 shown and described in connection with FIGS. 1-5, and preferably are constructed with the same dimensions given above. Two strips of wicking material 102, 104, such as glass fiber HEPA paper, are affixed to the underside of the base 12. The first strip 102 is positioned beneath the control well 82 and the first concentration chamber 96, and the second strip 104 is positioned beneath the specimen well 84 and the second concentration chamber 98.

With reference to the above description of the embodiment illustrated in FIGS. 8 and 9, in operation, a reagent, preferably chromium trioxide, is deposited into the detection well 86 and is absorbed by the glass fiber paper 98. A control sample and a sample of the biological fluid under test are deposited into the control and specimen wells 82, 84, respectively, using a swab, a pipet, or other fluid transfer means. Once inside the wells 82, 84, the control specimen is wicked across the first strip of paper 102 toward the first concentration chamber 96, and the sample of the biological fluid under test is wicked across the second strip of paper 104 toward the second concentration chamber 98. The strips 102, 104 volatilize the alcohol in the specimens and the vapors are focused upward by the concentration chambers 96, 98 through the passages 92, 94 in the detection well 86. Upon contact with the reagent, alcohol vapors contained in the volatilized control specimen will reduce the yellow chromium trioxide to blue chromic oxide, producing a blue spot in the detection well 86 above the first passage 92. Similarly, alcohol vapors volatilized from the sample of the biological fluid under test will reduce the reagent and produce a blue spot in the detection well 86 above the second passage 94. In this manner, rapid qualitative colorimetric detection of the presence of alcohol in either the control or biological specimen can be obtained.

Although the invention has been described with reference to specific embodiments, the description is intended to be illustrative of the invention and is not intended to be limiting. Various modifications, such as the dimensions of the test device and the amounts and types of chemicals used in the colorimetric analysis, may occur to those skilled in the art without departing form the true spirit and scope of the invention as defined in the appended claims.

What is claimed is:

1. A chemical analysis testing system for detecting the presence of a given chemical in a specimen of biological fluid, comprising:
    a swab having an absorbent head portion and a handle portion; and
    a test device, comprising:
        a base;
        a reagent retaining material secured to said base for storing a reagent which will give a visual indication if it is exposed to said given chemical;
        a concentration chamber below said reagent retaining material at least partially formed by the surfaces of said base, said chamber shaped so that any gases or vapors rising from the bottom of said chamber are concentrated by said surfaces as they rise;
        a passage between said concentration chamber and said reagent retaining material;
        a first well at least partially formed by the surfaces of said base for receiving said head of said swab after it has been saturated with biological fluid, said first well having a bottom surface which defines an opening, said first well being sized and shaped so as to wring said biological fluid from said head upon the insertion of said head into said first well and direct said wrungout biological fluid toward said opening;
        a strip of wicking material secured to said base interconnecting said opening and said concentration chamber, a portion of said strip forming the bottom of said concentration chamber, wherein said strip transports biological fluid from said opening to said bottom of said concentration chamber, said strip being chemically pre-treated with an agent which volatilizes said given chemical, so that if an amount of said given chemical is present in said biological fluid, said agent volatilizes said amount of said given chemical, causing at least a portion of said amount of said given chemical to rise from the bottom of said concentration chamber, whereupon said portion is concentrated by said surfaces of said base and is directed towards said passage and said reagent retaining material.

2. The testing system of claim 1, further comprising a second well for receiving and retaining said reagent retaining material and preventing spillage of said reagent.

3. The testing system of claim 2, wherein said strip of wicking material is formed from a substance which will not react with biological fluids or the given chemical, so as not to affect the reaction between the chemical with which the strip has been pre-treated and the given chemical.

4. The testing system of claim 3, wherein said strip of wicking material comprises glass fiber paper.

5. The testing system of claim 4, wherein said strip is pre-treated with potassium carbonate.

6. The testing system of claim 1, wherein said concentration chamber is of decreasing cross-section as the distance from the bottom of the chamber increases.

7. The testing system of claim 6, wherein said surfaces of said base forming said concentration chamber are hemispherical in shape.

8. A chemical analysis testing device for detecting the presence of a given chemical in a specimen of biological fluid, comprising:
    a base;
    a first well at least partially formed by the surfaces of said base for receiving a head of a swab after it has been saturated with biological fluid, said first well having a bottom surface which defines an opening, said first well being sized and shaped so as to wring said biological fluid from said head upon the insertion of said head into said first well and direct said wrungout biological fluid toward said opening;
    a second well;
    a reagent retaining material secured within for storing a reagent which will give a visual indication if it is exposed to said given chemical;
    a concentration chamber below said second well at least partially formed by the surfaces of said base, said chamber shaped so that any gases or vapors rising from the bottom of said chamber are concentrated by said surfaces as they rise;
    a passage between said concentration chamber and said second well;

a strip of wicking material secured to said base interconnecting said opening and said concentration chamber, a portion of said strip forming the bottom of said concentration chamber, wherein said strip transports biological fluid from said opening to said bottom of said concentration chamber, said strip being chemically treated with an agent which volatilizes said given chemical, so that if an amount of said given chemical is present in said biological fluid, said agent volatilizes said amount of said given chemical, causing at least a portion of said amount of said given chemical to rise from the bottom of said concentration chamber, whereupon said portion is concentrated by said surfaces of said base and is directed towards said passage and said reagent retaining material.

9. The chemical analysis testing device of claim 8, wherein said first well is further provided with an upper shelf for compressing the head of a swab as the swab is inserted into the first well under the shelf thereby releasing the biological fluid deposited on the head of the swab.

10. The chemical analysis testing device of claim 9, wherein said well further comprises a notch formed opposite said shelf for receiving and retaining the handle of said swab to lock said swab in place after the head of said swab has been inserted into said first well under said shelf.

11. A chemical analysis testing device for detecting the presence of a given chemical in a specimen of biological fluid, comprising:
  a base;
  a reagent retaining material secured to said base for storing a reagent which will give a visual indication if it is exposed to said given chemical;
  a first concentration chamber below said reagent retaining material at least partially formed by the surfaces of said base, said first chamber shaped so that any gases or vapors rising from the bottom of said first chamber are concentrated by said surfaces as they rise;
  a second concentration chamber below said reagent retaining material at least partially formed by the surfaces of said base, said second chamber shaped so that any gases or vapors rising from the bottom of said second chamber are concentrated by said surfaces as they rise;
  a first passage between said first concentration chamber and said reagent retaining material;
  a second passage between said second concentration chamber and said reagent retaining material;
  a first well at least partially formed by the surfaces of said base for receiving a test specimen of biological fluid, said first well having a bottom surface which defines a first opening, said first well being sized and shaped so as to direct said test specimen toward said first opening;
  a second well at least partially formed by the surfaces of said base for receiving a control specimen, said second well having a bottom surface which defines an opening, said second well being sized and shaped so as to direct said control specimen toward said second opening;
  a first strip of wicking material secured to said base interconnecting said first opening and said first concentration chamber, a portion of said first strip forming the bottom of said first concentration chamber, wherein said first strip transports said test specimen from said first opening to said bottom of said first concentration chamber, said first strip being chemically pre-treated with an agent which volatilizes said given chemical, so that if an amount of said given chemical is present in said test specimen, said agent volatilizes said amount of said given chemical, causing at least a portion of said amount of said given chemical to rise from the bottom of said first concentration chamber, whereupon said portion is concentrated by said surfaces of said first concentration chamber and is directed towards said first passage and said reagent retaining material; and
  a second strip of wicking material secured to said base interconnecting said second opening and said second concentration chamber, a portion of said second strip forming the bottom of said second concentration chamber, wherein said second strip transports said control specimen from said second opening to said bottom of said second concentration chamber, said second strip being chemically pre-treated with an agent which volatilizes said given chemical, so that if an amount of said given chemical is present in said control specimen, said agent volatilizes said amount of said given chemical, causing at least a portion of said amount of said given chemical to rise from the bottom of said second concentration chamber, whereupon said portion is concentrated by said surfaces of said second concentration chamber and is directed towards said second passage and said reagent retaining material, wherein comparison of the effect of the volatilized test specimen and the effect of the volatilized control specimen on the reagent retained by the reagent retaining material can be compared to help evaluate the validity of the results of the test on the test specimen.

12. The chemical analysis testing device of claim 11, wherein said first well is further provided with an upper shelf for compressing the head of a swab as the swab is inserted into the first well under the shelf thereby releasing the test specimen deposited on the head of the swab.

13. The chemical analysis testing device of claim 12, wherein said first well further comprises a notch formed opposite said shelf for receiving and retaining the handle of said swab to lock said swab in place after the head of said swab has been inserted into said first well under said shelf.

* * * * *